US012712083B2

(12) United States Patent
Shandilya et al.

(10) Patent No.: US 12,712,083 B2
(45) Date of Patent: Aug. 18, 2026

(54) TOOL FOR PREDICTING PROGNOSIS AND IMPROVING SURVIVAL OF PATIENTS

(71) Applicant: CERNER INNOVATION, INC., North Kansas City, MO (US)

(72) Inventors: Sumeet Shandilya, Bangalore (IN); S Rudresh, Kolar (IN); Ramadevi Kumaresan, Theni (IN); Praveen Bhat Gurpur, Bangalore (IN); Winston Dsouza, Uttara Kannada (IN)

(73) Assignee: CERNER INNOVATION, INC., Kansas City, MO (US)

( * ) Notice: Subject to any disclaimer, the term of this patent is extended or adjusted under 35 U.S.C. 154(b) by 282 days.

(21) Appl. No.: 18/065,478

(22) Filed: Dec. 13, 2022

(65) Prior Publication Data

US 2024/0194354 A1 Jun. 13, 2024

(51) Int. Cl.
*G16H 50/70* (2018.01)

(52) U.S. Cl.
CPC .................................. *G16H 50/70* (2018.01)

(58) Field of Classification Search
CPC ................................................ G06Q 50/20–26
USPC .......................................................... 705/2, 3
See application file for complete search history.

(56) References Cited

U.S. PATENT DOCUMENTS 11,942,219 B1 * 3/2024 McNair .................. G16H 40/63
2022/0270763 A1 * 8/2022 Schaeffer ............... G16B 20/20

OTHER PUBLICATIONS

Chen J et al. "A Survey on Applications of Artificial Intelligence in Fighting Against COVID-19". arXiv; 2021. From https://europepmc.org/article/ppr/ppr310589#R155. all pages. (Year: 2021).*
Sayed SA et al. "Applying Different Machine Learning Techniques for Prediction of COVID-19 Severity". IEEE Access. Sep. 28, 2021;9:135697-135707. doi: 10.1109/ACCESS.2021.3116067. PMID: 34786321; PMCID: PMC8545185. (Year: 2021).*
Ahmadi M et al. FWNNet: Presentation of a New Classifier of Brain Tumor Diagnosis Based on Fuzzy Logic and the Wavelet-Based Neural Network Using Machine-Learning Methods. Comput Intell Neurosci. Nov. 22, 2021;2021:8542637. doi: 10.1155/2021/8542637. PMID: 34853586. PMCID: PMC8629672. all pages (Year: 2021).*

(Continued)

*Primary Examiner* — Christopher L Gilligan
*Assistant Examiner* — Jessica Marie Webb
(74) *Attorney, Agent, or Firm* — Invoke

(57) ABSTRACT

A diagnostic and decision support technology is provided for determining the likely prognosis and potential treatment for patients experiencing a condition, such as COVID-19, for example. In particular, a mechanism is provided for receiving a historical patient dataset comprising one or more historical health parameters associated with a plurality of historical patients. Additionally, a patient dataset is received comprising one or more patient health parameters associated with a patient. A cluster is identified based on the similarity of the patient dataset and a plurality of historical patient datasets. From the cluster, a set of treatable features are identified and evaluated for their potential impact on the patient's successful recovery from the condition. A recommendation is generated based on the evaluation as to what feature should be treated first to decrease the mortality of the patient.

22 Claims, 8 Drawing Sheets

(56) References Cited

OTHER PUBLICATIONS

Pourhomayoun M et al. Predicting mortality risk in patients with COVID-19 using machine learning to help medical decision-making. Smart Health (AMST). Apr. 2021;20:100178. doi: 10.1016/j.smhl.2020.100178. Epub Jan. 16, 2021. PMID: 33521226; PMCID: PMC7832156. all pages. (Year: 2021).*

King et al., "Unsupervised Clustering of COVID-19 Chest X-Ray Images with a Self-Organizing Feature Map," 2020 IEEE 63rd International Midwest Symposium on Circuits and Systems (MWSCAS), Springfield, MA, USA, 2020, pp. 395-398, doi: 10.1109/MWSCAS48704.2020.9184493. all pages. (Year: 2020).*

S. K and S. Sarathambekai, "Machine Learning based Prediction Model for Health Care Sector—A Survey," 2021 Innovations in Power and Advanced Computing Technologies (i-PACT), Kuala Lumpur, Malaysia, 2021, pp. 1-7, doi: 10.1109/i-PACT52855.2021.9696646. all pages. (Year: 2021).*

Giuste et al., "Explainable Artificial Intelligence Methods in Combating Pandemics: A Systematic Review", Jun. 23, 2022, arXiv:2112.12705v4, https://doi.org/10.48550/arXiv.2112.12705, all pages. (Year: 2022).*

* cited by examiner

200

| Weight | Feature |
|---|---|
| 0.0052 ± 0.0004 | pneumonia |
| 0.0045 ± 0.0005 | covid_res |
| 0.0041 ± 0.0007 | age |
| 0.0028 ± 0.0008 | contact_other_covid |
| 0.0019 ± 0.0003 | intubed |
| 0.0008 ± 0.0004 | hypertension |
| 0.0003 ± 0.0002 | obesity |
| 0.0001 ± 0.0002 | copd |
| 0.0001 ± 0.0003 | diabetes |
| 0.0001 ± 0.0001 | renal_chronic |
| 0.0001 ± 0.0001 | cardiovascular |
| 0.0001 ± 0.0002 | inmspr |
| 0.0001 ± 0.0003 | tobacco |
| 0.0000 ± 0.0002 | other_disease |
| -0.0001 ± 0.0003 | asthma |
| -0.0016 ± 0.0004 | icu |
| -0.0016 ± 0.0004 | patient_type |
| -0.0018 ± 0.0006 | sex |
| -0.0020 ± 0.0005 | pregnancy |

202 204

TOOL FOR PREDICTING PROGNOSIS AND IMPROVING SURVIVAL OF PATIENTS

BACKGROUND

The corona virus disease 2019 (COVID-19) is discussed as merely one example of a potential use for the tool provided herein. The illness associated with COVID-19 has caused millions of infections and deaths since the beginning of its pandemic. Mortality in COVID-19 patients is governed by multiple factors, including age, gender, co-morbidities, and more. When a COVID-19 patient is brought into the hospital, there is a quick clinical assessment of the patient including lab tests to decide the immediate course of action. During this assessment, multiple parameters are captured. These parameters not only give an indication of the patient's status at that point in time, but also hold clues to the prognosis (e.g., predictions of recovery versus mortality) of the patient. Some of these parameters may have a greater bearing (e.g., weightage) on the prognosis than others, though many if not most parameters that may have such an impact have not been evaluated or may even not have been identified.

Multiple clinical studies of COVID-19 patients have shown that certain factors such as advanced age, obesity, male gender and comorbidities such as hypertension, diabetes, and others confer higher susceptibility to severe disease and death in COVID-19 patients relative to other factors. This provides an avenue for building a tool that can clearly predict the mortality rate in the given patient, and help to focus medical attention on controlling those factors with the highest impact on mortality/survival. Since timely decisions can save lives in critically ill patients, the tool can help mobilize medical resources to reduce mortality and increase survival.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter. In brief and at a high level, this disclosure describes, among other things, methods, systems, computer storage media, and graphical user interfaces for a computer application having a tool that leverage machine learning techniques to predict survival/mortality rates of a patient based on analyzing the patient's clinical parameters and other patient's clinical parameters and outcomes, while also pointing to those parameters with the greatest impact on increasing survival and decreasing mortality, for example.

The tool assists caregivers in reducing mortality rates of critically ill COVID-19 patients, leading to reduced burden and savings to the extent of hundreds of millions of dollars on the healthcare system. Healthcare providers will be able to achieve better outcomes for patients, leading to enhanced patient goodwill. Current technological systems are presented with a problem that is solved by the technical portions of this disclosure. When a system receives a large group of data related to a particular disease or illness, current systems are unable to identify clusters of patients with similar features related to that illness and then identify that feature is the most likely to reduce the chances of mortality if treated. As such, the current technology provides a system, method, and computer readable media that accurately determines a plurality of clusters for a historical patient dataset. It then uses machine learning and other algorithms to identify a feature within the cluster related to the current patient that most likely will reduce the mortality of that current patient.

BRIEF DESCRIPTION OF THE DRAWINGS

The present technology is described in detail below with reference to the attached drawing figures, wherein.

DETAILED DESCRIPTION

Figure 1:
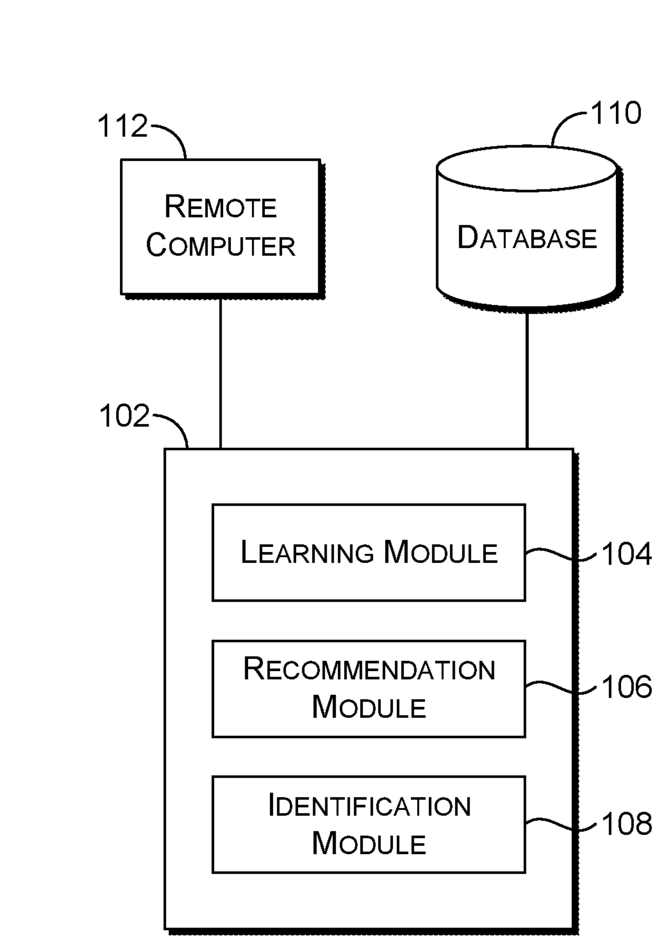
FIG. 1 depict aspects of an illustrative architecture suitable for practicing an embodiment of the disclosure.

The subject matter of the present technology is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our disclosure may be embodied as, among other things: a method, system, or set of instructions embodied on one or more computer readable media. Accordingly, the embodiments may take the form of a hardware embodiment, a software embodiment, or an embodiment combining software and hardware. In one embodiment, the present disclosure takes the form of a computer-program product that includes computer-usable instructions embodied on one or more computer readable media.

Computer-readable media include both volatile and nonvolatile media, removable and non-removable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or non-transitory storage devices. These technologies can store data momentarily, temporarily, or permanently.

In brief and at a high level, this disclosure describes, among other things, methods, systems, computer storage media, and graphical user interfaces for providing computerized, machine-learning driven decision support services. By way of a high level example, systems and methods are provided for receiving a historical patient dataset comprising one or more historical health parameters associated with a plurality of historical patients. Such historical health parameters may be health related data, demographic data, behavioral data, patient history, family health history, other related information, or any combination thereof that has been captured and digitally encoded for multiple patients that have been previously associated with a particular condition, such as COVID, independent of the patients' outcome. Additionally, a patient dataset is received comprising one or more patient health parameters associated with a particular patient, such that the patient health parameters digitally encoded in the dataset are specific to the particular patient. Such parameters related to the particular patient are current or "up-to-date" according to the data and information that is available within a database. Such information may include data, as available, related to the information obtained with the historical patient dataset.

In embodiments, a machine learning unsupervised algorithm may generate a plurality of clusters based on the one or more historical health parameters associated with the plurality of historical patients and the health parameters associated with the patient dataset. The machine learning unsupervised algorithm may then identify which cluster of the plurality of clusters is associated with the patent dataset. For example, the machine learning unsupervised algorithm can identify one cluster that the patient dataset is most similar to, or which the cluster is predicted to be most relevant for the patient dataset, based on the historical parameter(s) in the cluster relative to the health parameter(s) in the patient dataset. Next, one or more treatable health parameters in that cluster are ranked relative to each other based on each treatable health parameter's effect on a mortality of each of the historical patients. For example, health parameters that are treatable and which are associated with an increase in survival/decrease in mortality for a condition may be ranked higher than other health parameters that are treatable but which are associated with an increase in mortality/decrease in survival. Based on the ranking of the one or more treatable health parameters within the particular cluster identified as a best fit to the patient data set by the machine learning unsupervised algorithm, a recommendation is generated for at least one treatable health parameter for the patient from the one or more treatable health parameters within the particular cluster identified. For example, one or more treatments that correspond to one or more of the highest ranked treatable health parameters may be identified by the application and provided as a recommendation for treatment of the patient associated with the dataset. Once the recommended treatment is performed or an indication is received by the application that the treatment will/has been performed, the current patient dataset may be updated by the machine learning unsupervised algorithm and processed by the machine learning unsupervised algorithm into a new cluster to identify one or more additional ("next") health parameter(s) to be evaluated for treatment recommendations.

In various embodiments, a historical patient dataset comprising one or more time-independent historical health parameters and one or more time-dependent historical health parameters associated with a plurality of historical patients is received via the application having the machine learning unsupervised algorithm. As used herein, "time-independent historical health parameters" refers to health parameters which are measured at different time intervals while "time-dependent historical health parameters" refers to health parameters which are not measured in time intervals. Using a transformation of the time-dependent historical health parameters and/or a fuzzy logic algorithm in various embodiments, the one or more time-dependent historical health parameters are converted into one or more newly "converted" or "transformed" time-independent historical health parameters via the application. Further, an analytical patient dataset is generated comprising the one or more time-independent historical health parameters and the one or more newly converted time-independent historical health parameters. Based on the one or more time-independent historical health parameters and the one or more converted time-independent historical health parameters associated with the plurality of historical patients now aggregated or combined within the analytical patient dataset, a plurality of clusters is generated by the machine learning unsupervised algorithm. Next, one or more treatable health parameters is identified from the one or more time-independent historical health parameters and the one or more converted time-independent historical health parameters within each of the plurality of clusters. One or more treatable health parameters is ranked for each cluster of the plurality of clusters based on each treatable health parameter's effect on a mortality of each of the historical patients in each cluster of the plurality of clusters. As such, the machine learning unsupervised algorithm is trained using historical time-independent and time-dependent health parameters from historical patient data.

Subsequently, when a patient dataset may be received comprising one or more patient health parameters associated with a patient, the application having the machine learning unsupervised algorithm identifies a particular patient cluster from the plurality of clusters generated (e.g., previously generated, or as re-generated to include the received patient dataset), where that patient cluster is determined to be associated with, relevant to, or a best match/fit for the patient dataset as determined by the machine learning unsupervised algorithm. Finally, based at least in part on the patient cluster identified and the ranking of the one or more treatable health parameters (e.g., previously ranked, or as re-ranked after ingestion of the received patient dataset), a recommendation for a particular treatment of at least one of the one or more treatable health parameters is generated for the patient by the application. The particular treatment recommended corresponds, generally, to one or more of the treatable health parameters having the highest or a higher ranking relative to the ranking of other treatable health parameters in the particular cluster.

Beginning with FIG. 1, a system environment 100 is depicted that includes a system 102. The system 102 includes a memory and one or more processors coupled to the memory (not shown) for executing computer-executable instructions stored on computer-readable storage media, such as memory. In some aspects, the system 102 comprises a utility or application, whether run locally or web-based, that performs backend (e.g., user-invisible) operations and functions to automatically determine patient-specific or "smart" recommendations for patient education instructions.

System 102 typically includes therein, or has access to, a variety of computer-readable media, for instance, database cluster 110. Computer-readable media can be any available media that might be accessed by system 102, and includes volatile and nonvolatile media, as well as, removable and non-removable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium that can be used to store the desired information that may be accessed by the control server. Combinations of any of the above also may be included within the scope of computer-readable media.

The computer storage media discussed above and illustrated in FIG. 1, including database cluster 110, provide storage of computer-readable instructions, data structures, program modules, and other data for the system 102. In some embodiments, database cluster 110 takes the form of a cloud-based data store, and in some embodiments is accessible by a cloud-based computing platform.

The system 102 might operate in a computer network using logical connections to one or more remote computers 112. Remote computers 112 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 112 might also be physically located in nontraditional medical care environments so that the entire healthcare community might be capable of integration on the network. The remote computers 112 might be personal computers, servers, routers, network PCs, peer devices, other common network nodes, or the like and might comprise some or all of the elements described above in relation to the system 102. The devices can be personal digital assistants or other like devices.

In some embodiments, remote computers 112 comprise computing-devices that are part of a cloud-computing platform. In some embodiments, remote computers 112 are associated with a health records, data source such as an electronic health record (EHR) system of a hospital or medical organization, a health information exchange EHR, insurance provider EHR, ambulatory clinic EHR, or patient-sensor, or other data source, and facilitates accessing data of the source and communicating the data to system 102 and/or other computing devices on a cloud computing platform, including other remote computers.

In operation, an organization might enter commands and information into the system 102 or convey the commands and information to the system 102 via one or more of the remote computers 112 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the system 102. In addition to a monitor, the system 102 and/or remote computers 112 might comprise other peripheral output devices, such as speakers and a printer.

The system 102 includes a learning module 104. In some aspects, the learning module 104 receives a set of patient or other type of data from the database cluster 110. Such database cluster may include an EHR which contains the records of individuals that have been diagnosed or presumed to have a particular illness and/or condition. In one instance, the particular illness may be COVID-19 or any other disease for which data has been collected. The historical data received by the learning module 104 may contain a number of measured parameters for each patient within the dataset. Such historical parameters may include demographic data, personal health data, biometric data, and/or other types of data, factors, and/or parameters which are described in more detail below. The historical dataset received may be a structured or an unstructured dataset, in some embodiments, representing a plurality of individuals that have been diagnosed or presumed to have a particular illness and/or condition. An additional dataset is received for a new or current patient. The current patient dataset contains information related to the health, demographics, and/or other related information that is up-to-date or current for the patient. The current patient dataset is combined with the historical data received from the database cluster 110 to create a combined dataset. As such, the learning module 104 may autonomously create a set of clusters for the combined dataset, wherein the current patient is also autonomously assigned to a cluster within the set of clusters by the learning module 104.

In embodiments, the learning module 104 may assemble or restructure an unstructured dataset into a structured or organized dataset. In such embodiments, the learning module 104 operates as a machine learning unsupervised learning module. As mentioned, the organized dataset may include all or a portion of the data from the unstructured dataset. The organized dataset may include one or more instances formed by organizing data elements of the dataset using joins, cross products, and/or other unsupervised learning techniques, as described herein. The organized dataset can be a combined data warehouse, which comprises multiple data marts. The learning module 104 can suggest, define, and/or create data marts, identifying the constituent parts or the like, by combining and analyzing features of disparate tables or other data sources. The process of assembling an organized dataset from the unstructured dataset may include defining relationships (e.g., connections, distances, and/or confidences) between data elements of the unstructured dataset using a plurality of unsupervised learning techniques. In general, unsupervised learning techniques attempt to discover structure in unstructured or semi-structured data.

Optionally, the learning module 104 may provide output results (e.g., probabilities, connections, distances, instances, or the like) that inform or populate a probabilistic graph database, a metadata layer for a probabilistic graph database, or the like. The learning module 104 may populate other data structures, displays, visualizations, or the like with output results.

In various embodiments, the unsupervised learning module 208 is configured to assemble the unstructured dataset into multiple versions of an organized dataset. For instance, the learning module 104 can assemble tens, hundreds, or thousands of versions of organized datasets. Each version can be assembled using a unique combination of unsupervised learning techniques and thus each version may identify different relationships between data elements of the dataset. Additionally or alternatively, the learning module 104 can assemble two or more versions of organized datasets using the same combination of unsupervised learning techniques, but by varying the parameters, key concepts, or business objectives used by the unsupervised learning techniques. As such each version of the organized datasets may be substantially different. Furthermore, the learning module 104 can assemble each of these versions of the organized dataset based only on a subset or sample of the unstructured dataset, as previously described, such that each version is an organized, trial dataset. By assembling a large number of datasets in this way without regard to accuracy, the probability that an accurate dataset is developed increases.

In one embodiment, the learning module 104 includes a clustering algorithm. The clustering algorithm can be configured to perform one or more clustering analyses on the unstructured data or dataset. Clustering involves the algorithm autonomously grouping a set of objects in the data in such a way that objects/data in the same group ("cluster") are more similar, in at least one sense, to each other than to those in other clusters. Non-limiting examples of clustering algorithms include hierarchical clustering, k-means algorithm, kernel-based clustering algorithms, density-based clustering algorithms, spectral clustering algorithms. In an embodiment, the clustering algorithm utilizes decision tree clustering with pseudo labels to generate a plurality of clusters from the unstructured data or dataset. In an embodiment, the clustering algorithm utilizes decision tree clustering with pseudo labels to generate a plurality of clusters from structured data or dataset. The clustering algorithm may use focal points, clusters, and/or the like to determine relationships between, distances between, and/or confidences for data points or objects in the data. By using focal points, clustering, or the like to break up large amounts of data, the learning module 104 may efficiently determine relationships, distances, and/or confidences for the data.

As mentioned, the learning module 104 may utilize multiple unsupervised learning techniques to assemble an organized dataset. In one embodiment, the learning module 104 uses at least one clustering algorithm or other clustering machine-learning technique to assemble each organized dataset. In other embodiments, some organized datasets may be assembled without using a clustering technique. In some aspects, the clustering technique is used to cluster the historical dataset received from the database cluster 110. Additionally, the clustering technique is used to cluster the historical dataset in combination with the patient dataset. The learning module 104 may adjust, reorganized, or regenerated a plurality of clusters based on the number of desired parameters of similarity. For example, one set of data may be clustered using a set of 10 parameters of similarity. The degree of similarity that is used when generating clusters may be defined by a user or may be a default value of the learning module 104, and/or may be modified. As such, the degree of similarity defines a minimum or a threshold quantity of parameters that are to be the same or similar to each other in order to form or generate a distinct cluster, and the degree of similarity may be adjusted manually or adjusted automatically by the learning module 104.

Additionally, the learning module 104 may provide enhanced decision support by using properties like collaboration, persistence, mobility and distributed operation, autonomy, adaptability, knowledge and intelligence, reactive and proactive capability, reuse, scalability, reliability, maintainability, security, fault-tolerance, trust, and other primary properties. In addition, numerous secondary properties of multi-agents in embodiments may facilitate decision support, including: reasoning, planning, and learning capabilities; decentralization; conflict resolution; distributed problem solving; divide-and-conquer strategies for handling complex problems; location transparency; allowing for competing objects to be represented; goal-driven or data-driven including agent-to-agent or user-to-agent; time-driven; support for multiple layers of abstraction above services thereby providing flexibility, adaptability, and reuse and simplification; negotiation; hierarchies having dynamic self-organization; abilities to spawn and destroy agents as needed; utilization of transient and persistent data; abilities to address uncertain, missing or inconsistent data; sensitivity to resource and time constraints; ontology-driven functionality; flexible run time invocation and planning; obligations; ability to act to achieve objectives on behalf of individuals and organizations; organizational influence; and other secondary properties. Examples of agents, which may be used by the multi-agent systems of embodiments of our technologies, include: Interface agents; planning agents; information agents; adapter wrapper agents; filter agents; discovery agents; task agents; blackboard agents; learning agents, including supervised learning, unsupervised learning, reinforcement learning, for example; observer agents; inference agents; communication agents; directory agents; administrator and security agents; facilitator agents; mediator agents; and agent solvers. Agent solvers can include, for example: Markov decision processing; approximate linear programming; natural language extraction solvers (e.g., nCode, NLP, or MLP solvers); fuzzy-neural networks, logistic and linear regression; forward-chaining inference (e.g., data-driven); backward-chaining inference (e.g., goal-driven); inductive inference; genetic algorithm; neural network including with genetic algorithm for training; stochastic; self-organizing Kohenen map; Q-learning; quasi-Newton; gradient; decision trees; lower/higher bound search; constrain satisfaction; Naives Bayes fuzzy; LP-solver including mixed integer multi-variable min/max solvers; Finite State Machine and HFSM; temporal difference reasoning; data mining for classification, clustering, learning and prediction; K-means; support vector machines; K-nearest neighbor classification; Tanimoto distance; C5.0; a priori; EM, simulated annealing, Tabu search, multi-criteria decision making, evolutionary algorithm, and other such solvers known by one skilled in the art.

Continuing, the system 102 includes a ranking module 106. In some aspects, the ranking module 106 can evaluate the features within each cluster. Such evaluation may be done in connection with the learning module 104. In this evaluation, the ranking module 106 and learning module 104 determine the effect of or identify which feature (or combination of features) within a given cluster may lead to an increase in the mortality of a patient for a particular illness or condition, and/or an increase in survivable of a patient for that same particular illness or condition. The ranking module 106 evaluates the combination of features within the cluster and for each historical patient within the cluster to determine or predict the likelihood that the new patient within the cluster is to survive. Such evaluation may use a K-nearest neighbor algorithm, a self-organizing map, a combination of the two, or any other algorithm that may evaluate the features for each patient within the cluster along with compare the current patient cluster with other clusters within the plurality of clusters.

In one example, the clustering technique may produce a cluster that includes the current patient dataset and data for a plurality of the historical patients. The data related to the historical patients contains health related information along with each historical patient's outcome, such as a mortality of the patient or a recovery from the particular illness or condition. By evaluating this data within the one cluster, the ranking module 106 is able to determine what particular combination of features contributes to the mortality or the survival of a patient having the particular illness or condition. A K-nearest neighbor algorithm may be used in combination with a self-organizing map to evaluate the statistical probability that the current patient is predicted to survive (e.g., a survival rate) based on the features and outcomes of the historical patients in the cluster to which the new patient has been sorted or grouped. This may be based on the evaluation of the varied parameters (parameters and features may be used interchangeably herein) and the combinations of parameters found for each historical patient within the cluster, in embodiments. For example, the K-nearest neighbor and self-organizing map may determine that a set of parameters is common among patients who failed to recover from a particular illness, i.e., wherein the outcome is mortality. The ranking module 106 may use a permutation of importance algorithm to determine the most important permutations that contribute to mortality or identify which features contribute the most to mortality. By using the machine learning algorithms, various permutations and combinations may be discovered within the cluster that are not discoverable by human observation due to a human oversight, human dismissal, bias, or human incapability.

The ranking module 106 may rank each of the features found within the cluster based on the identified and determined contribution to mortality. The ranking module 106 may also identify features that are treatable such as pneumonia, blood pressure, or other treatable features, as distinguishable from non-treatable features. The ranking module 106 may also identify features that are not treatable such as sex, age, pregnancy status, etc. The ranking module 106 may rank features relative to one another that the ranking model 106 determines are most critical or contribute to morality the most from the entirety of the features found within the cluster. The criticality of the features are determined using machine learning algorithms which compare all the features for each patient within the cluster and the various outcomes. The ranking module 106 may also rank only the features that are treatable based on their effect on the mortality of historical patients, in some embodiments.

Continuing, the system 102 includes a recommendation module 108, in various aspects. In some aspects, the recommendation module 108 retrieves one or more rankings from the ranking module 106. This ranking may contain at least one treatable feature or condition that is ranked as most contributory to the potential mortality of the current patient. The ranking may also contain a feature that is most likely to reduce the mortality of the current patient if treated (e.g., a highest ranked feature). The recommendation module 108, in various aspects, can communicate the identified feature that, if treated, is most likely to increase the mortality of the current patient. The feature is communicated for display, with or without a treatment corresponding to the highest ranked feature in some embodiments.

Regarding FIG. 1, it should be understood that the placement of various components is an abstraction such that one or more of the various components may be located or may operate anywhere within the system environment 100, and as such, the depicted arrangement is only an example. Accordingly, other components and arrangements may be used additionally or instead of that which is depicted, such that one or more depicted components may be omitted, for example. Further, the components shown may be implemented as discrete components, distributed components, or in conjunction with other components, and in any suitable combination and physical or virtual location. The functions described herein as being performed by one or more components, entities, and/or devices may be carried out by hardware, firmware, and/or software, in embodiments, such that the functions are not limited unless explicitly described as such.

It should also be understood that the system environment 100 shown in FIG. 1 is only one example of a suitable environment, and this example has been simplified for ease of discussion. Accordingly, other components not shown may also be included within the environment, and one or more of the shown component may be omitted, in various embodiments. Each of the components of FIG. 1 may be implemented using any type or number of computing devices, in embodiments. The components may communicate with each other directly or, for example, indirectly via a network, including one or more of a telecommunication network, a local area network (LANs), a wide area network (WANs), and/or a peer-to-peer-network. Such networking environments may include campus-wide or enterprise-wide computer networks, intranets, and the Internet. It should be understood that any number of components shown in FIG. 1 may be employed within the system environment 100 within the scope of the present invention. Each may be implemented via a single device or multiple devices cooperating in a distributed environment.

Figure 2:
FIG. 2 depicts an exemplary dataset in accordance with an embodiment of the disclosure.

Turning now to FIG. 2, there is shown one example embodiment of a feature set 200 comprised of a combination of specific features corresponding to one or more patients within the historical patient dataset. The number of features that are identified or found for a patient within the historical patient dataset is not limited and the feature set 200 should be seen as an example and not limiting. The features column 204 may identify the features that are found within a cluster or found within a particular patient's dataset. As described above, the features found within a cluster are evaluated to determine which feature(s) contribute most to the increased morality of patients within that cluster. This evaluation may produce an output of a weighting 202. For example, the feature of pneumonia is found with the features column 204 and is shown to have the highest weight. This may signify that pneumonia is predicted to be the feature, within that cluster, that contributes the greatest to the increased morality of patients within that cluster.

The features column 204 may contain a plurality of features that are treatable or un-treatable, in aspects. Features that are un-treatable can be included as the non-treatable features may provide insights into potential illness-related insights, for example, during evaluation and ranking of treatable features. For example, if a majority of patients who succumb to the particular illness are overweight, such information may be used to promote the increased inoculation of the overweight population.

The various features of the features column 204 may include demographics data points and values that define features such as age, race, nationality, gender, address; medical history such as immunization history. Pre-existing conditions, non-communicable diseases, medical procedures previously performed, medications are also potential features. Family history; social history such as alcoholism, smoking, occupation; history of present illness such as how many days after onset of symptoms did the patient get admitted, what were the presenting symptoms; vital parameters on day of admission may also be features included. The features column may also contain lab values and BDMI values such as partial oxygen pressure (sequential organ failure assessment (SOFA) Indicator), fraction of inspired oxygen (SOFA Indicator), Platelets (SOFA Indicator), Glasgow Coma Score (SOFA Indicator), Bilirubin (SOFA Indicator), Mean arterial pressure (SOFA Indicator), Creatinine/urine output (SOFA Indicator), D-dimer, Lactate dehydrogenase, Blood gases, C-reactive protein blood test results, Radiology results, X rays, CT scan, MRI scan, U/S scan, Fluoroscopy. Additionally, the features column 204 may contain information related to a patients admission to the ICE and which day of admission to the ICE. Further, the features column 204 may contain information related to if a ventilator used, the final outcome for the patient such as recovery or mortality. Finally if recovery is indicated—after how many days was patient shifted out of ICU and if mortality is indicated, what was cause of death.

Figure 3:
FIG. 3 an exemplary dataset in accordance with an embodiment of the disclosure.
Figure 3:
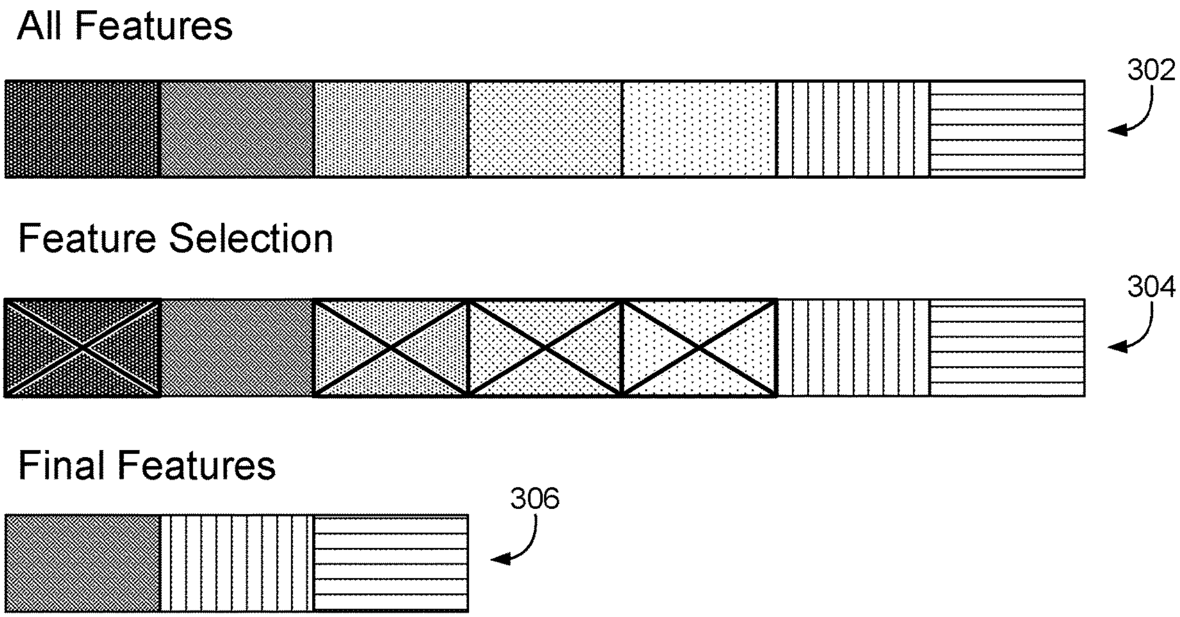

Turning to FIG. 3, a sample feature evaluation and reduction 300 is depicted in accordance with an embodiment. Initially, all of the features 302 are evaluated based on their impact on the morality of patients within a cluster. For example, a cluster may contain 100 patients and each patient within that cluster is associated with seven features (e.g., parameter pattern shared among the patients in the cluster). Each feature is evaluated, as described above, to determine what impact that feature had or did not have in contributing to the increased mortality of one or more of the patients in the cluster. Features not selected in the feature selection 304 may be non-treatable features, in some embodiments. The final features 306 that were evaluated and selected (being a reduced set) are then ranked based on their impact on the morality of the patients with the highest being the most impactful on morality.

Figure 4:
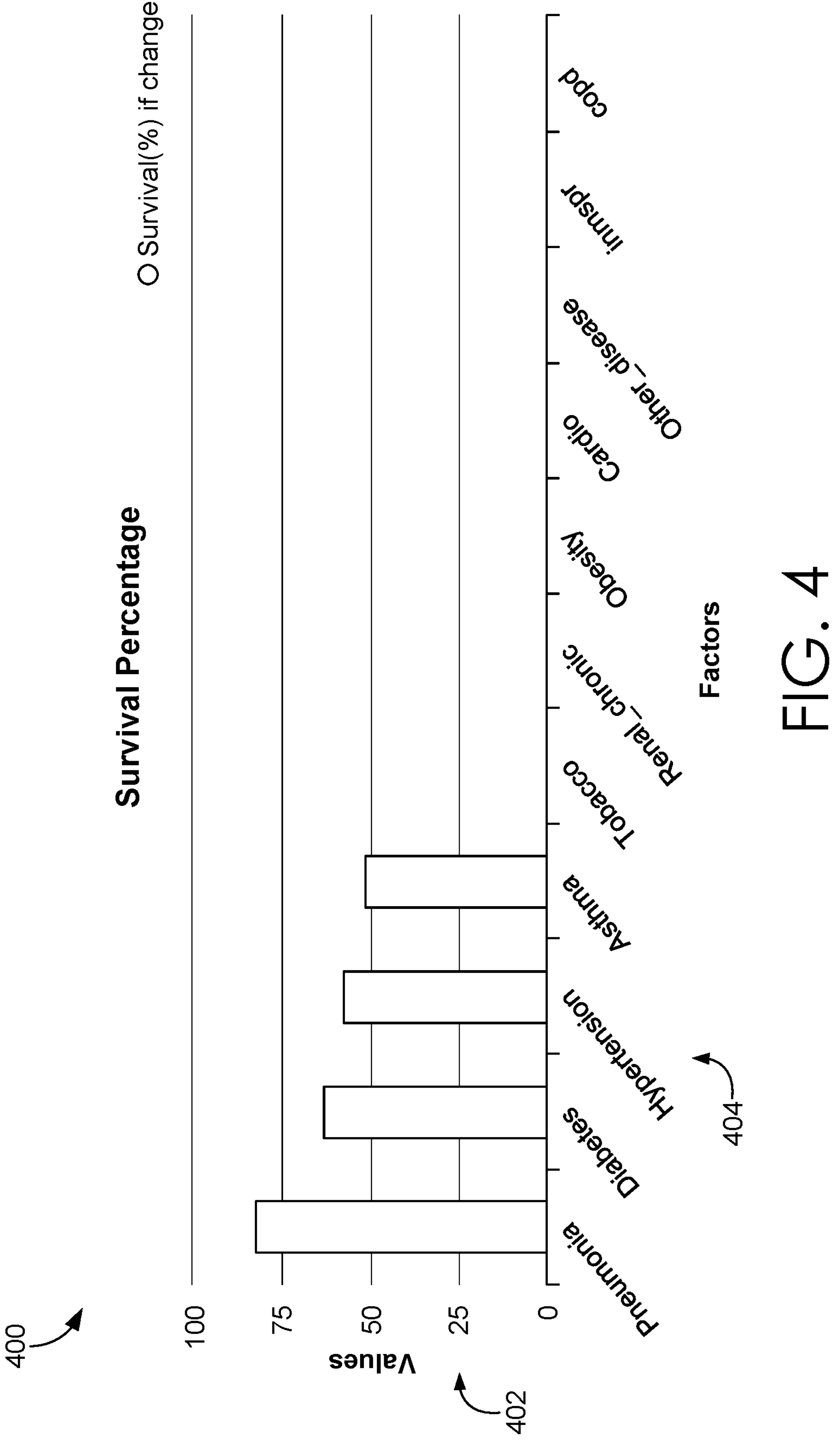
FIG. 4 an exemplary dataset in accordance with an embodiment of the disclosure.

Turning now to FIG. 4, an exemplary graph 400 is provided illustrating an embodiment. Graph 400 is a visual depiction of the outcome of an evaluation of various features 404 for a particular cluster. The modules described above evaluate the features 404 using machine learning algorithms to determine the survival percentage 402 if the feature is changed. For example, an algorithm such as the K-nearest neighbor, self-organizing map, dimensionality reduction, principal component analysis, linear discriminant analysis, or any neural network may be used to determine the potential outcome of a current patient if a particular feature is changed. As shown in graph 400, by changing a feature, such as reduction in the presence of pneumonia, for a current patient, that patient may have the chances of survival increase.

Figure 5:
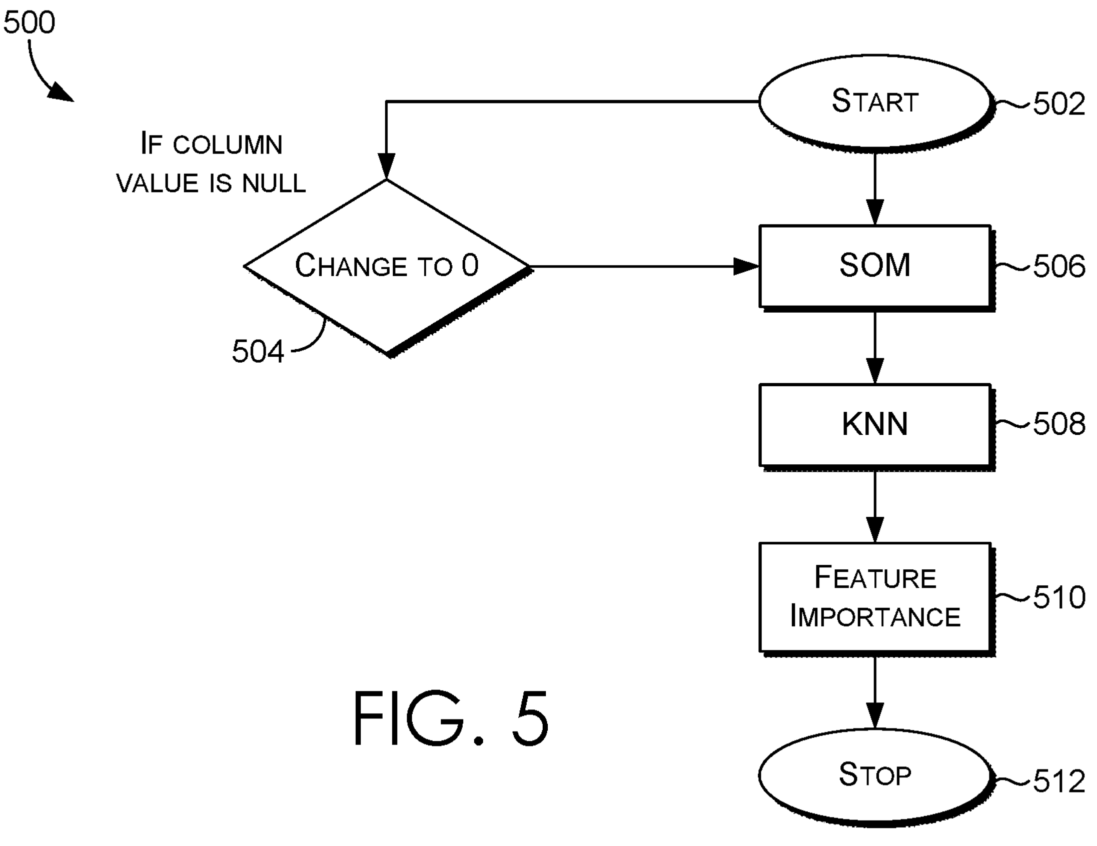
FIG. 5 depicts a flowchart of an exemplary method, in accordance with an aspect of the present disclosure.

FIG. 5 that provides a flow diagram 500 of a particular embodiment. At step 502, a historical patient dataset is received from a data store such as database cluster 110. This data includes historical patient data related to a plurality of patients that may have been diagnosed with a particular illness such as COVID-19. Additionally, a current patient dataset is received that includes data associated with a current patient that is being treated for the particular illness. Such data may be used along with a clustering algorithm such as an unsupervised learning model to determine a plurality of clusters for the combination of the historical patient dataset and the current patient dataset. The current patient is assigned to one of the plurality of clusters. If the dataset does not include any data that is time-dependent, the clustering may occur without any data manipulation. However, if the data includes time-dependent data, the clustering may occur subsequent to step 504 or subsequent to other data manipulation.

At step 504, the set of data may contain features that may be stationary (e.g., static and fixed; time-independent) or non-stationary (e.g., dynamic, changing over time; time-dependent). To properly assess or evaluate non-stationary features, an algorithm is used to convert the non-stationary features into a waveform to be evaluated using a frequency domain algorithm. For example, if a patient's blood sugar level fluctuates over time, such a measurement may not be input into the current model as such, and must be converted to values that may be input into the current model such that the dataset may be clustered. This time dependent data or non-stationary data, found in the historical data and/or in the current patient dataset, may be evaluated using a conversion algorithm as described in more detail below. Such an algorithm may use fuzzy logic and other frequency algorithms to convert the time-dependent data into time-independent data. Once the time-dependent data in the dataset is converted, the entire dataset may be clustered and the current patient may be assigned to a cluster.

At step 506, a self-organizing map is created for the features found within the cluster to be evaluated that contains the current patient dataset. Further, at step 508, a K-nearest neighbor algorithm is run on the features within the self-organizing map. Once the features are evaluated with the K-nearest neighbor at step 510, the features are ranked based on their impact on the mortality of the historical patients. Each feature is evaluated to determine its impact on the mortality of the historical patients. Additionally, a combination of features is identified that lead to increased mortality can be determined, in some embodiments. Following the evaluation of the impact on mortality of the features within the cluster, the features are then ranked based on their impact on mortality, as previously discussed. Additionally, the ranking may be a combination of. It may be determined that the potential projected increase in survival for the current patient is due to a feature that is reduced or treated.

At step 512, a recommendation is generated based on the ranking of the features within the cluster and the current patient. The recommendation may be to treat the top ranked feature and may also provide the increased survivability percentage if that treatment is performed. A clinician may then receive the recommendation and provide appropriate treatment to reduce or remove the feature from the current patient. For example, if the recommendation were to show that "pneumonia" is the top ranked feature, the clinician may treat the current patient for pneumonia. Upon being treated for pneumonia, the current patient may be re-introduced at step 502 with the treated feature removed from the current patient dataset. As such, the current patient will be assigned to a new cluster via the machine learning algorithm and the process can be performed again to find the next feature to be treated.

Figure 6:
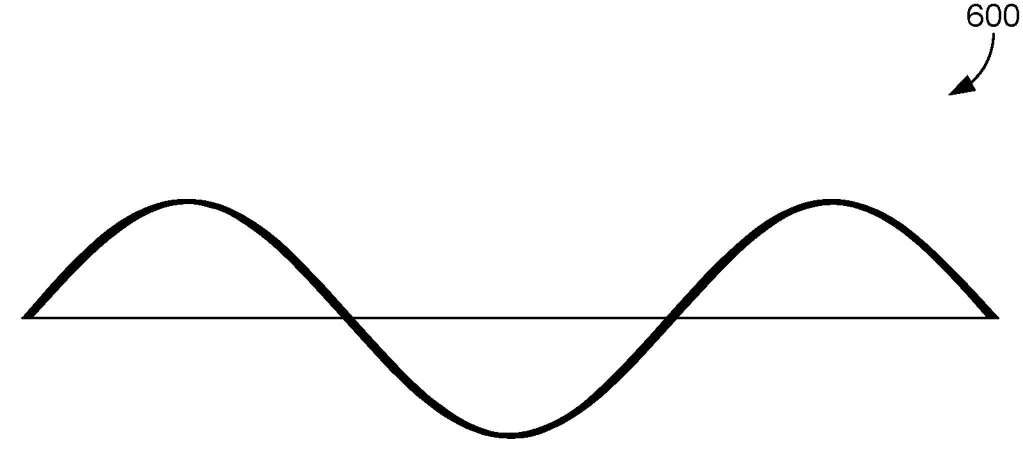
FIG. 6 depicts an exemplary graph of data in accordance with an embodiment of the disclosure.

Continuing with FIG. 6, it provides a depiction of an exemplary set of data in accordance with an embodiment. Many times within a medical analysis, data is presented using a binary value of either a 1 or a 0, to represent whether the patient has a feature or does not. Many situations, however, require an evaluation of the feature that is represented by changes over time, such that a binary value may not be the best representation for the feature. For example, two patients with diabetes may present with blood sugar levels at very different values, as those values can be measured but will change over both short periods of time (e.g., glucose measured over hours) and long periods of time (e.g., A1C measurements over years). In order to accurately utilize, ingest, and evaluate time-dependent data via the algorithms described herein, the data is transformed into a usable data type, being time-independent data. Further, each diagnosis or feature, such as kidney disease, may be based on several data measurements obtained over a period of time and the measurements may indicate levels of severity of the diagnosis or feature. As such, there is a need to produce a single time-independent value that accurately describes the dynamic and fluctuating values of some features in detail.

As seen in FIG. 6, data can be plotted over time, where time is the x-axis and the value of the feature is the y-axis. As such, our initial data received may be plotted as a time-dependent set of data and modeled using sin and cos functions. The time-dependent data is then converted into a frequency domain using a Fourier transform, in some embodiments. For a given feature, many different datasets may be produced that contribute to that feature. For example, a diagnosis of diabetes may have several measurable datasets over a large period of time. Each dataset is converted from time-domain to frequency domain, in such an example. An analysis may then be run on the frequency domain data for each dataset within for the feature. The analysis is taking statistical features of a range of periods for each dataset of the feature. Such statistical features may be mean, median, or standard deviation. Further, a mean of the total based on the ranges measured is calculated. Once this analysis is performed, the output is analyzed using fuzzy logic that may output a value from −1 to 1. With the feature now being described using a single value in that accurately represents the dynamic feature, the new/converted value for the dynamic feature may be successfully used in the algorithms described herein.

Figure 7:
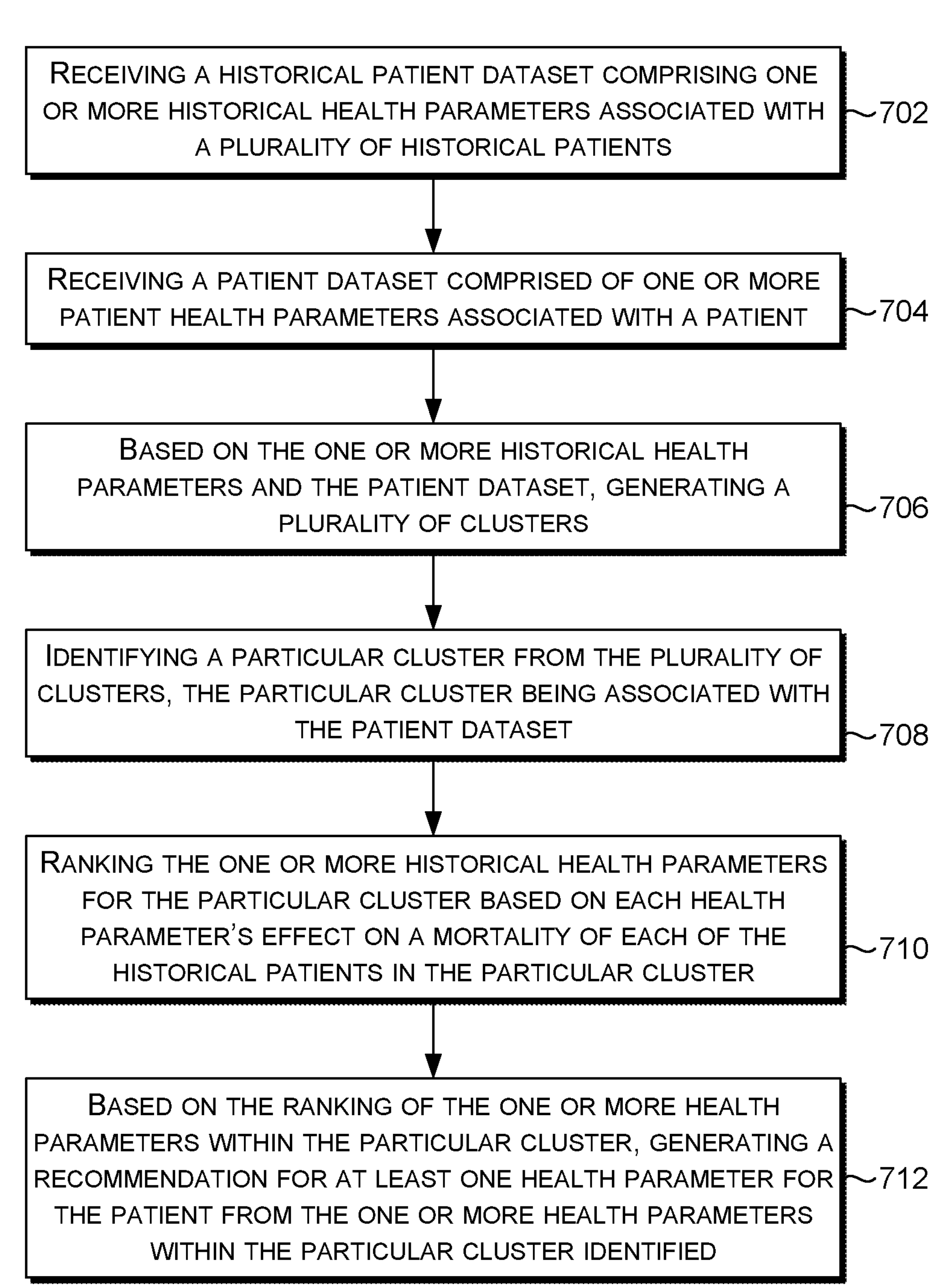
FIG. 7 depicts a flowchart of an exemplary method, in accordance with an aspect of the present disclosure.

FIG. 7 provides a method 700 that provides aspects in accordance with an embodiment. Beginning at step 702, the system receives a historical patient dataset comprising one or more historical health parameters associated with a plurality of historical patients. Continuing with step 704, receiving a patient dataset comprised of one or more patient health parameters associated with a patient. In step 706, based on the one or more historical health parameters and the patient dataset, generating a plurality of clusters. Step 708 provides for identifying a particular cluster from the plurality of clusters, the particular cluster being associated with the patient dataset. Moving on to step 710, ranking the one or more historical health parameters for the particular cluster based on each health parameter's effect on a mortality of each of the historical patients in the particular cluster. Finally, at step 712, based on the ranking the one or more historical health parameters within the particular cluster, generating a recommendation for at least one health parameter for the patient from the one or more health parameters within the particular cluster.

Figure 8:
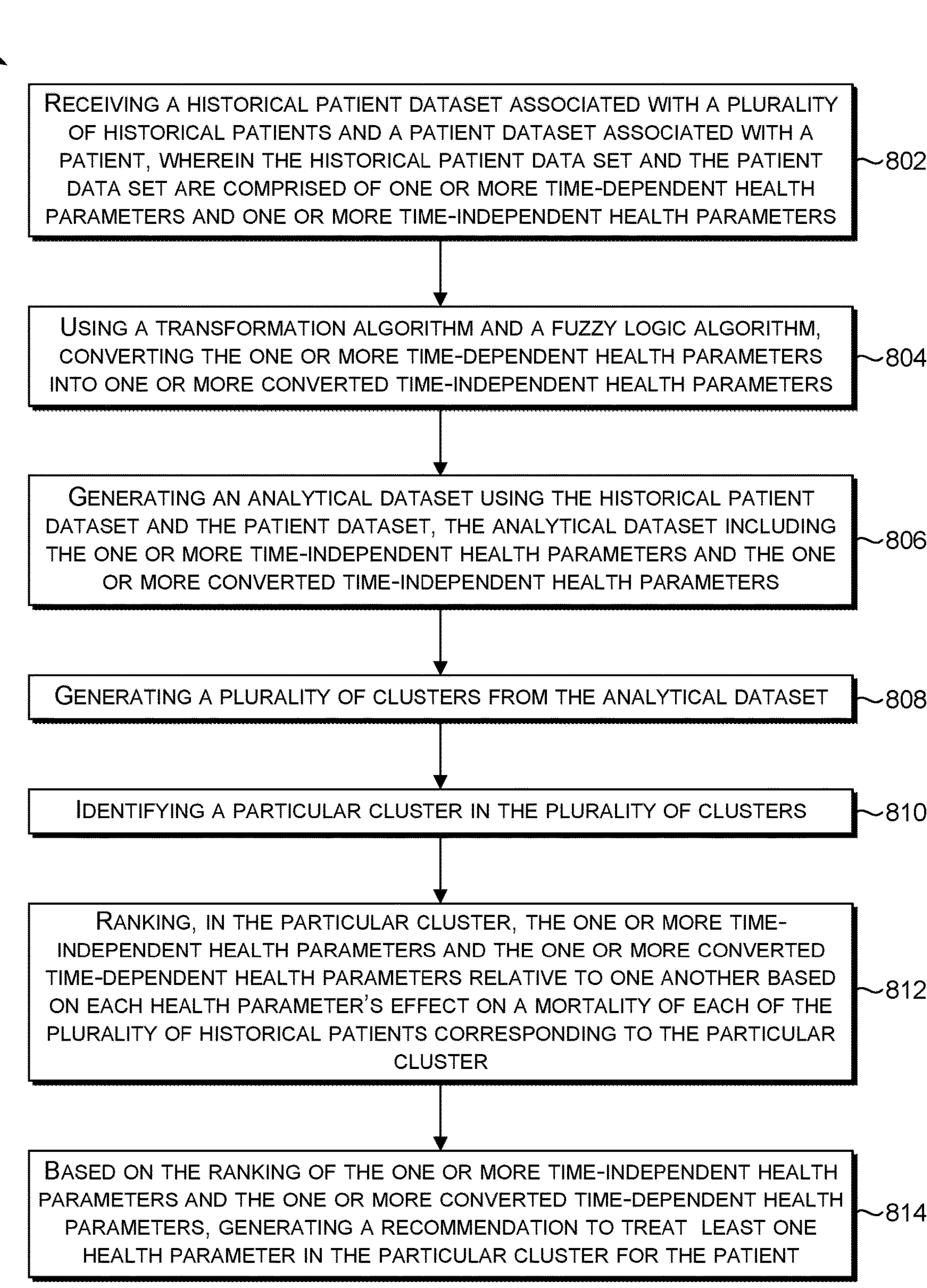
FIG. 8 depicts a flowchart of an exemplary method, in accordance with an aspect of the present disclosure.

Moving to FIG. 8 provides a method 800 that provides aspects in accordance with an embodiment described herein. Beginning at step 802, receiving a historical patient dataset associated with a plurality of historical patients and a patient dataset associated with a patient, wherein the historical patient data set and the patient data set are comprised of one or more time-dependent health parameters and one or more time-independent health parameters. Step 804 uses a transformation algorithm and a fuzzy logic algorithm and converts the one or more time-dependent health parameters into one or more converted time-independent health parameters. Further, at step 806, generates an analytical dataset using the historical patient dataset and the patient dataset, the analytical dataset including the one or more time-independent health parameters and the one or more converted time-independent health parameters. In step 808, a plurality of clusters from the analytical dataset is generated. Step 810 includes identifying a particular cluster in the plurality of clusters. Step 812 ranks, in the particular cluster, the one or more time-independent health parameters and the one or more converted time-dependent health parameters relative to one another based on each health parameter's effect on a mortality of each of the plurality of historical patients corresponding to the particular cluster. Finally, at step 814 based on the ranking of the one or more time-independent health parameters and the one or more converted time-dependent health parameters, generating a recommendation to treat least one health parameter in the particular cluster for the patient.

Figure 9:
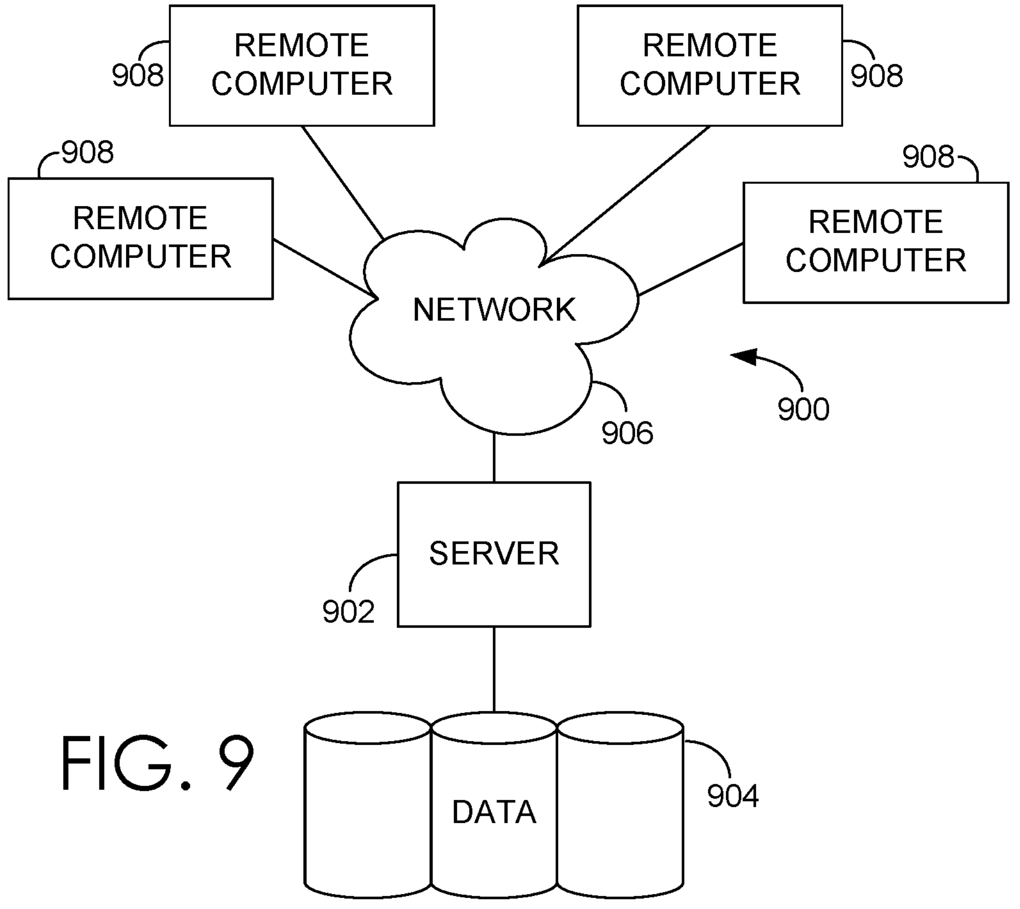
FIG. 9 illustratively provides an example embodiment of a computer program routine.

Turning now to FIG. 9, a computing environment 900 that is suitable for use in implementing aspects of the present invention is depicted. The computing environment 900 is merely an example of one suitable computing environment and is not intended to suggest any limitation as to the scope of use or functionality of the invention. Neither should the computing environment 900 be interpreted as having any dependency or requirement relating to any single component or combination of components illustrated therein. Generally, in aspects, the computing environment 900 is a medical-information computing-system environment. However, this is just one example and the computing environment 900 can be operational with other types, other kinds, or other-purpose computing system environments or configurations. Examples of computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

In aspects, the computing environment 900 can be described in the general context of computer instructions, such as program modules, applications, and/or extensions, being read and executed by a computing device. Examples of computer instructions can include routines, programs, objects, components, and/or data structures that perform particular tasks or implement particular abstract data types. The aspects discussed herein can be practiced in centralized and/or distributed computing environments, i.e., where computer tasks are performed utilizing remote processing devices that are linked through a communications network, whether hardwired, wireless, or a combination thereof. In a distributed configuration, computer instructions might be stored or located in association with one or more local and/or remote computer storage media (e.g., memory storage devices). Accordingly, different portions of computer instructions for implementing the computer tool in the computing environment 900 may be executed and run on different devices, whether local, remote, stationary, and/or mobile.

With continued reference to FIG. 9, the computing environment 900 comprises a computing device 902, shown in the example form of a server. Although illustrated as one component in FIG. 9, the present invention can utilize a plurality of local servers and/or remote servers in the computing environment 900. The computing device 902 can include components such as a processing unit, internal system memory, and a suitable system bus for coupling to various components, including electronic storage, memory, and the like, such as a data store, a database, and/or a database cluster. Example components of the computing device 902 include a processing unit, internal system memory, and a suitable system bus for coupling various components, including a data store 904, with the computing device 902. An example system bus might be any of several types of bus structures, including a memory bus or memory controller, a peripheral bus, and a local bus, using any of a variety of bus architectures. Examples of bus architectures include Industry Standard Architecture (ISA) bus, Micro Channel Architecture (MCA) bus, Enhanced ISA (EISA) bus, Video Electronics Standards Association (VESA®) local bus, and Peripheral Component Interconnect (PCI) bus, also known as Mezzanine bus.

The computing device 902 includes or has access to a variety of non-transitory computer-readable media. Computer-readable media can be any available media that is locally and/or remotely accessible by the computing device 902, and includes volatile, nonvolatile, removable, and non-removable media. By way of example, and not limitation, computer-readable media can comprise computer storage media and communication media. Computer storage media includes volatile, nonvolatile, removable, and non-removable media, as implemented in any method or technology for storage of information, such as computer-readable instructions, data structures, program modules, or other data.

The computing device 902 can include or can have access to computer-readable media. Computer-readable media can be any available media that can be accessed by computing device 902, and includes volatile and nonvolatile media, as well as removable and non-removable media. By way of example, and not limitation, computer-readable media can include computer storage media and communication media.

Computer storage media can include, without limitation, volatile and nonvolatile media, as well as removable and non-removable media, implemented in any method or technology for storage of information, such as computer-readable instructions, data structures, program modules, or other data. In this regard, computer storage media can include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium that can be used to store the desired information and that can be accessed by the computing device 902. Computer storage media does not comprise signals per se.

Communication media typically embodies computer-readable instructions, data structures, program modules, or other data in a modulated data signal, such as a carrier wave or other transport mechanism, and can include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also can be included within the scope of computer-readable media.

The computing device 902 might operate in a network 906 using logical connections to one or more remote computers 908. In some aspects, the one or more remote computers 908 can be located at a variety of locations, such as medical facilities, research environments, and/or clinical laboratories (e.g., molecular diagnostic laboratories), as well as hospitals, other inpatient settings (e.g., surgical centers), veterinary environments, ambulatory settings, medical billing offices, financial offices, hospital administration settings, home healthcare environments, and/or clinicians' offices). As used herein, "clinicians," "medical professionals," or "healthcare providers" can include: physicians; specialists such as surgeons, radiologists, cardiologists, and oncologists; emergency medical technicians; physicians' assistants; nurse practitioners; health coaches; nurses; nurses' aides; pharmacists; dieticians; microbiologists; laboratory experts; laboratory technologists; genetic counselors; researchers; veterinarians; students; and the like.

In aspects, the computing device 902 uses logical connections to communicate with one or more remote computers 908 within the computing environment 900. In aspects where the network 906 includes a wireless network, the computing device 902 can employ a modem to establish communications with the Internet, the computing device 902 can connect to the Internet using Wi-Fi or wireless access points, or the server can use a wireless network adapter to access the Internet. The computing device 902 engages in two-way communication with any or all of the components and devices illustrated in FIG. 9, using the network 906. Accordingly, the computing device 902 can send data to and receive data from the remote computers 908 over the network 906.

The network 906 is a computer network that can include local area networks (LANs) and/or wide area networks (WANs), in some aspects. The network 906 can include wireless and/or physical (e.g., hardwired) connections. Examples of networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. When the network 906 includes a WAN-type configuration, the computing device 902 might comprise a modem or other means for establishing communications over the WAN, such as the Internet, in such aspects. As such, the network 906, can provide the components and devices access to the Internet and web-based applications.

The network 906 can include an entity-wide network, campus-wide network, an office-wide network, an enterprise-wide networks, and the Internet. In the network 906, applications, extensions, program modules or portions thereof might be stored in association with the computing device 902, the data store 904, and any of the one or more remote computers 908. For example, various application programs can reside on the memory associated with any one or more of the remote computers 908. In the computing environment 900 that is illustrated as being a distributed configuration of the network 906, the components and devices can communicate with one another and can be linked to each other using a network 906. It will be appreciated by those of ordinary skill in the art that the network connections shown are exemplary and other means of establishing a communications link between the computers (e.g. computing device 902 and remote computers 908) might be utilized.

In operation, an organization might enter commands and information into the computing device 902 or convey the commands and information, for example, directly in peer-to-peer or near-field communication, or through the network 906 using telecommunications or Wi-Fi, to the computing device 902 via one or more of the remote computers 908 through input devices, such as a keyboard, a pointing device (e.g., a mouse), a trackball, as stylus, or a touch pad. Other input devices comprise microphones, satellite dishes, scanners, or the like. Commands and information might also be sent directly from a remote healthcare device to the computing device 902. In addition to a screen, monitor, or touchscreen component, the computing device 902 and/or remote computers 908 might comprise other peripheral output devices, such as speakers and printers.

The computing environment 900 includes one or more remote computers 908 that may be accessed by the computing device 902 over the network 906 or directly using peer-to-peer connections or mesh networking, in various aspects. The remote computers 908 might be servers, routers, network personal computers, peer devices, network nodes, computing devices, personal digital assistants, personal mobile devices, medical devices, patient monitoring equipment, or the like, and might comprise some or all of the elements described above in relation to the computing device 902. The one or more remote computers 908 can include multiple computing devices, in various aspects. In aspects where the network 906 is distributed in configuration, the one or more remote computers 908 can be located at one or more different geographic locations. In an aspect where the one or more remote computers 908 are a plurality of computing devices, each of the plurality of computing devices can be located across various locations such as buildings in a campus, medical and research facilities at a medical complex, offices or "branches" of a banking/credit entity, or can be mobile devices that are wearable or carried by personnel, or attached to vehicles or trackable items in a warehouse, for example. In some aspects, the remote computers 908 are physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. The remote computers 908 might also be physically located in nontraditional healthcare environments so that the entire healthcare community might be capable of integration on the network 906. In other aspects, the remote computers 908 can be physically located in a non-medical setting, such as a packing and shipping facility or deployed within a fleet of delivery or courier vehicles.

Continuing, the computing environment 900 includes a data store 904. Although shown as a single component, the data store 904 can be implemented using multiple data stores that are communicatively coupled to one another, independent of the geographic or physical location of a memory device. The data store 904 can, for example, store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. The data store 904 can, for example, also store data in the form of electronic records, such as electronic medical records of patients, patient-specific documents and historical records, transaction records, billing records, task and workflow records, chronological event records, and the like. Generally, the data store 904 includes physical memory that is configured to store information encoded in data. For example, the data store 904 can provide storage for computer-readable instructions, computer-executable instructions, data structures, data arrays, computer programs, applications, and other data that supports the functions and actions to be undertaken using the computing environment 900 and components shown in the example of FIG. 9.

As shown in the example of FIG. 9, when the computing environment 900 operates with distributed components that are communicatively coupled via the network 906, computer instructions, applications, extensions, and/or program modules can be located in local and/or remote computer storage media (e.g., memory storage devices). Aspects of the present invention can be described in the context of computer-executable instructions, such as program modules, being executed by a computing device. Program modules can include, but are not limited to, routines, programs, objects, components, and data structures that perform particular tasks or implement particular abstract data types. In aspects, the computing device 902 can access, retrieve, communicate, receive, and update information stored in the data store 904, including program modules. Accordingly, the computing device 902 can execute, using a processor, computer instructions stored in the data store 904 in order to perform aspects described herein.

Although internal components of the devices in FIG. 9, such as the computing device 902, are not illustrated, those of ordinary skill in the art will appreciate that internal components and their interconnection are present in the devices of FIG. 9. Accordingly, additional details concerning the internal construction device are not further disclosed herein. Although many other internal components of the computing device 902 and the remote computers 908 are not shown, such components and their interconnection are known. Accordingly, additional details concerning the internal construction of the computing device 902 and the remote computers 908 are not further disclosed herein.

Additionally, it will be understood by those of ordinary skill in the art that the computing environment 900 is just one example of a suitable computing environment and is not intended to limit the scope of use or functionality of the present invention. Similarly, the computing environment 900 should not be interpreted as imputing any dependency and/or any requirements with regard to each component and combination(s) of components illustrated in FIG. 9. It will be appreciated by those having ordinary skill in the art that the connections illustrated in FIG. 9 are also examples as other methods, hardware, software, and devices for establishing a communications link between the components, devices, systems, and entities, as shown in FIG. 9, can be utilized in implementation of the present invention. Although the connections are depicted using one or more solid lines, it will be understood by those having ordinary skill in the art that the example connections of FIG. 9 can be hardwired or wireless, and can use intermediary components that have been omitted or not included in FIG. 9 for simplicity's sake. As such, the absence of components from FIG. 9 should be not be interpreted as limiting the present invention to exclude additional components and combination(s) of components. Moreover, though devices and components are represented in FIG. 9 as singular devices and components, it will be appreciated that some aspects can include a plurality of the devices and components such that FIG. 9 should not be considered as limiting the number of a device or component.

Regarding FIGS. 1 through 9, it will be understood by those of ordinary skill in the art that the environment(s), system(s), and/or methods(s) depicted are not intended to limit the scope of use or functionality of the present embodiments. Similarly, the environment(s), system(s), and/or methods(s) should not be interpreted as imputing any dependency and/or any requirements with regard to each component, each step, and combination(s) of components or step(s) illustrated therein. It will be appreciated by those having ordinary skill in the art that the connections illustrated the figures are contemplated to potentially include methods, hardware, software, and/or other devices for establishing a communications link between the components, devices, systems, and/or entities, as may be utilized in implementation of the present embodiments. As such, the absence of component(s) and/or steps(s) from the figures should be not be interpreted as limiting the present embodiments to exclude additional component(s) and/or combination(s) of components. Moreover, though devices and components in the figures may be represented as singular devices and/or components, it will be appreciated that some embodiments can include a plurality of devices and/or components such that the figures should not be considered as limiting the number of a devices and/or components.

It is noted that embodiments of the present invention described herein with reference to block diagrams and flowchart illustrations. However, it should be understood that each block of the block diagrams and/or flowchart illustrations can be implemented in the form of a computer program product, an entirely hardware embodiment, a combination of hardware and computer program products, and/or apparatus, systems, computing devices/entities, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code can be performed sequentially such that one instruction is retrieved, loaded, and executed at a time. In some embodiments, retrieval, loading, and/or execution can be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

Additionally, as should be appreciated, various embodiments of the present disclosure described herein can also be implemented as methods, apparatus, systems, computing devices/entities, computing entities, and/or the like. As such, embodiments of the present disclosure can take the form of an apparatus, system, computing device, computing entity, and/or the like executing instructions stored on a computer-readable storage medium to perform certain steps or operations. However, embodiments of the present disclosure can also take the form of an entirely hardware embodiment performing certain steps or operations.

Many different arrangements of the various components depicted, as well as components not shown, are possible without departing from the scope of the claims below. Embodiments of our technology have been described with the intent to be illustrative rather than restrictive. Alternative embodiments will become apparent readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. A computer-implemented method performed by at least one device including a hardware processor, the computer-implemented method comprising:

training a neural network, implemented using an unsupervised machine learning algorithm, to identify one or more treatable health parameters, wherein training the neural network comprises:

accessing, via a network connection by a multi-agent system comprising multiple artificial intelligence agents (multiple AI agents), a database cluster that comprises an electronic health record system (EHR system) that is remote from the multi-agent system, the EHR system storing patient medical records in disparate data sources in a variety of locations that are remote from one another;

receiving, by the multi-agent system from the disparate data sources of the EHR system via the network connection, a historical patient dataset associated with a plurality of historical patients, wherein the historical patient dataset comprises one or more historical time-dependent health parameters and one or more historical time-independent health parameters, the one or more historical time-dependent health parameters comprising multiple historical blood test measurements obtained over a period of time;

converting, by the multi-agent system, the one or more historical time-dependent health parameters of the historical patient dataset into one or more converted historical time-independent health parameters using a transformation algorithm and a fuzzy logic algorithm;

generating, by the multi-agent system, multiple thousands of versions of an analytical dataset using the historical patient dataset, the analytical dataset including the one or more historical time-independent health parameters and the one or more converted historical time-independent health parameters, wherein generating the multiple thousands of versions of the analytical dataset comprises using different combinations of unsupervised learning algorithms to define different relationships between data elements of the analytical dataset amongst the multiple thousands of versions of the analytical dataset;

populating, by the multi-agent system, a probabilistic graph database with the different relationships between the data elements of the analytical dataset amongst the multiple thousands of versions of the analytical dataset;

generating, by the unsupervised machine learning algorithm of the neural network, a plurality of clusters from the multiple thousands of versions of the analytical dataset using the different relationships between the data elements of the analytical dataset amongst the multiple thousands of versions of the analytical dataset from the probabilistic graph database, wherein populating the probabilistic graph database and generating the plurality of clusters comprise modifying a graph-based data structure that encodes probabilistic relationships between health parameters across the multiple thousands of versions of the analytical dataset;

identifying, using the unsupervised machine learning algorithm of the neural network, sets of treatable historical health parameters that correspond respectively to the plurality of clusters; and ranking, using the unsupervised machine learning algorithm of the neural network, the one or more historical time-independent health parameters and the one or more converted historical time-independent health parameters relative to one another respectively within the corresponding sets of treatable historical health parameters based on each treatable historical health parameter's effect on a mortality of each of the plurality of historical patients corresponding to the respective clusters of the corresponding sets of treatable historical health parameters;

receiving, by the multi-agent system from the EHR system via the network connection, a particular patient dataset associated with a particular patient, wherein the particular patient dataset comprises one or more particular time-dependent health parameters and one or more particular time-independent health parameters, the one or more particular time-dependent health parameters comprising multiple particular blood test measurements obtained over a period of time;

identifying, using the unsupervised machine learning algorithm of the neural network, a particular cluster in the plurality of clusters that is associated with the particular patient based on a measure of similarity between the health parameters of the particular patient and the health parameters of the particular cluster; and initiating a treatment for the particular patient based on at least one treatable historical health parameter in the particular cluster, wherein initiating the treatment comprises:

generating a recommendation to treat the at least one treatable historical health parameter in the particular cluster for the particular patient based on the ranking of the one or more historical time-independent health parameters and the one or more converted historical time-independent health parameters; and communicating the recommendation to a computing device for display on the computing device.

2. The computer-implemented method of claim 1, further comprising identifying one or more treatable health parameters from the one or more historical time-independent health parameters and the one or more converted historical time-independent health parameters within the particular cluster.

3. The computer-implemented method of claim 1, further comprising generating a survival percentage of each one or more time-independent health parameters and the one or more converted historical time-independent health parameters, the survival percentage being generated based on an effect treatment of each of the health parameters is predicted to have on the particular patient associated with the particular patient dataset.

4. The computer-implemented method of claim 1, further comprising modeling the one or more historical time-dependent historical health parameters and the one or more particular time-dependent health parameters using sine and cosine functions.

5. The computer-implemented method of claim 1, wherein:

the multiple AI agents of the multi-agent system comprise a first agent solver, a second agent solver, a third agent solver, and a fourth agent solver;

wherein the first agent solver comprises a fuzzy neural network, converting the one or more historical time-dependent health parameters of the historical patient dataset into one or more converted historical time-independent health parameters comprises:

converting the one or more historical time-dependent health parameters from time-dependent data in a time domain to time-independent data in a frequency domain using a Fourier transform; and the first agent solver executing the fuzzy logic algorithm using the fuzzy neural network; and wherein the second agent solver generates the plurality of clusters from the multiple thousands of versions of the analytical dataset using a clustering algorithm;

wherein the ranking the one or more historical time-independent health parameters and the one or more converted historical time-independent health parameters comprises:

the third agent solver creating a self-organizing map for the one or more historical time-independent health parameters and the one or more converted historical time-independent health parameters; and the fourth agent solver running a K-nearest neighbor algorithm on the one or more historical time-independent health parameters and the one or more converted historical time-independent health parameters within the self-organizing map to perform an evaluation of the one or more historical time-independent health parameters and the one or more converted historical time-independent health parameters.

6. The computer-implemented method of claim 1, wherein the at least one treatable historical health parameter comprises pneumonia and further comprising treating the particular patient for pneumonia.

7. The computer-implemented method of claim 1, wherein converting the one or more historical time-dependent health parameters of the historical patient dataset into the one or more converted historical time-independent health parameters further comprises:

converting the one or more historical time-dependent health parameters from time-dependent data in a time domain to time-independent data in a frequency domain using a Fourier transform algorithm;

computing one or more statistical measures of the time-independent data in the frequency domain; and generating the one or more converted historical time-independent health parameters based at least on the one or more statistical measures of the time-independent data using the fuzzy logic algorithm.

8. One or more non-transitory computer-readable storage media storing computer-useable instructions that, when used by one or more computing devices, cause the one or more computing devices to perform a method, the method comprising:

training a neural network, implemented using an unsupervised machine learning algorithm, to identify one or more treatable health parameters, wherein training the neural network comprises:

accessing, via a network connection by a multi-agent system comprising multiple artificial intelligence (AI) agents, a database cluster that comprises an EHR system that is remote from the multi-agent system, the EHR system storing patient medical records in disparate data sources in a variety of locations that are remote from one another;

receiving, by the multi-agent system from the disparate data sources of the EHR system via the network connection, a historical patient dataset associated with a plurality of historical patients, wherein the historical patient dataset comprises one or more historical time-dependent health parameters and one or more historical time-independent health parameters, the one or more historical time-dependent health parameters comprising multiple historical blood test measurements obtained over a period of time;

converting, by the multi-agent system, the one or more historical time-dependent health parameters of the historical patient dataset into one or more converted historical time-independent health parameters using a transformation algorithm and a fuzzy logic algorithm;

generating, by the multi-agent system, multiple thousands of versions of an analytical dataset using the historical patient dataset, the analytical dataset including the one or more historical time-independent health parameters and the one or more converted historical time-independent health parameters, wherein generating the multiple thousands of versions of the analytical dataset comprises using different combinations of unsupervised learning algorithms to define different relationships between data elements of the analytical dataset amongst the multiple thousands of versions of the analytical dataset;

populating, by the multi-agent system, a probabilistic graph database with the different relationships between the data elements of the analytical dataset amongst the multiple thousands of versions of the analytical dataset;

generating, by the unsupervised machine learning algorithm of the neural network, a plurality of clusters from the multiple thousands of versions of the analytical dataset using the different relationships between the data elements of the analytical dataset amongst the multiple thousands of versions of the analytical dataset from the probabilistic graph database, wherein populating the probabilistic graph database and generating the plurality of clusters comprise modifying a graph-based data structure that encodes probabilistic relationships between health parameters across the multiple thousands of versions of the analytical dataset;

identifying, using the unsupervised machine learning algorithm of the neural network, sets of treatable historical health parameters that correspond respectively to the plurality of clusters; and ranking, using the unsupervised machine learning algorithm of the neural network, the one or more historical time-independent health parameters and the one or more converted historical time-independent health parameters relative to one another respectively within the corresponding sets of treatable historical health parameters based on each treatable historical health parameter's effect on a mortality of each of the plurality of historical patients corresponding to the respective clusters of the corresponding sets of treatable historical health parameters;

receiving, by the multi-agent system from the EHR system via the network connection, a particular patient dataset associated with a particular patient, wherein the particular patient dataset comprises one or more particular time-dependent health parameters and one or more particular time-independent health parameters, the one or more particular time-dependent health parameters comprising multiple particular blood test measurements obtained over a period of time;

identifying, using the unsupervised machine learning algorithm of the neural network, a particular cluster in the plurality of clusters that is associated with the particular patient based on a measure of similarity between the health parameters of the particular patient and the health parameters of the particular cluster; and initiating a treatment for the particular patient based on at least one treatable historical health parameter in the particular cluster, wherein initiating the treatment comprises:

generating a recommendation to treat the at least one treatable historical health parameter in the particular cluster for the particular patient based on the ranking of the one or more historical time-independent health parameters and the one or more converted historical time-independent health parameters; and communicating the recommendation to a computing device for display on the computing device.

9. The one or more non-transitory computer-readable storage media of claim 8, further comprising identifying one or more treatable health parameters from one or more historical time-independent health parameters and the one or more converted historical time-independent health parameters within the particular cluster.

10. The one or more non-transitory computer-readable storage media of claim 8, further comprising generating a survival percentage of each one or more time-independent health parameters and the one or more converted historical time-independent health parameters, the survival percentage being generated based on an effect treatment of each of the health parameters is predicted to have on the particular patient associated with the particular patient dataset.

11. The one or more non-transitory computer-readable storage media of claim 8, further comprising modeling the one or more historical time-dependent health parameters and the one or more particular time-dependent health parameters using sine and cosine functions.

12. The one or more non-transitory computer-readable storage media of claim 11, wherein the transformation algorithm is a Fourier transform algorithm of the sine and cosine functions.

13. The one or more non-transitory computer-readable storage media of claim 8, wherein the at least one treatable historical health parameter comprises pneumonia.

14. A system comprising:

one or more processors, that by executing computer readable instructions stored in memory, perform:

training a neural network, implemented using an unsupervised machine learning algorithm, to identify one or more treatable health parameters by at least:

accessing, via a network connection by a multi-agent system comprising multiple artificial intelligence (AI) agents, a database cluster that comprises an EHR system that is remote from the multi-agent system, the EHR system storing patient medical records in disparate data sources in a variety of locations that are remote from one another;

receiving, by the multi-agent system from the disparate data sources of the EHR system via the network connection, a historical patient dataset associated with a plurality of historical patients, wherein the historical patient dataset comprises one or more historical time-dependent health parameters and one or more historical time-independent health parameters, the one or more historical time-dependent health parameters comprising multiple historical blood test measurements obtained over a period of time;

converting, by the multi-agent system, the one or more historical time-dependent health parameters of the historical patient dataset into one or more converted historical time-independent health parameters using a transformation algorithm and a fuzzy logic algorithm;

generating, by the multi-agent system, multiple thousands of versions of an analytical dataset using the historical patient dataset, the analytical dataset including the one or more historical time-independent health parameters and the one or more converted historical time-independent health parameters, wherein generating the multiple thousands of versions of the analytical dataset comprises using different combinations of unsupervised learning algorithms to define different relationships between data elements of the analytical dataset amongst the multiple thousands of versions of the analytical dataset;

populating, by the multi-agent system, a probabilistic graph database with the different relationships between the data elements of the analytical dataset amongst the multiple thousands of versions of the analytical dataset;

generating, by the unsupervised machine learning algorithm of the neural network, a plurality of clusters from the multiple thousands of versions of the analytical dataset using the different relationships between the data elements of the analytical dataset amongst the multiple thousands of versions of the analytical dataset from the probabilistic graph database, wherein populating the probabilistic graph database and generating the plurality of clusters comprise modifying a graph-based data structure that encodes probabilistic relationships between health parameters across the multiple thousands of versions of the analytical dataset;

identifying, using the unsupervised machine learning algorithm of the neural network, sets of treatable historical health parameters that correspond respectively to the plurality of clusters; and ranking, using the unsupervised machine learning algorithm of the neural network, the one or more historical time-independent health parameters and the one or more converted historical time-independent health parameters relative to one another respectively within the corresponding sets of treatable historical health parameters based on each treatable historical health parameter's effect on a mortality of each of the plurality of historical patients corresponding to the respective clusters of the corresponding sets of treatable historical health parameters;

receiving, by the multi-agent system from the EHR system via the network connection, a particular patient dataset associated with a particular patient, wherein the particular patient dataset comprises one or more particular time-dependent health parameters and one or more particular time-independent health parameters, the one or more particular time-dependent health parameters comprising multiple particular blood test measurements obtained over a period of time;

identifying, using the unsupervised machine learning algorithm of the neural network, a particular cluster in the plurality of clusters that is associated with the particular patient based on a measure of similarity between the health parameters of the particular patient and the health parameters of the particular cluster; and initiating a treatment for the particular patient based on at least one treatable historical health parameter in the particular cluster, wherein initiating the treatment comprises:

generating a recommendation to treat the at least one treatable historical health parameter in the particular cluster for the particular patient based on the ranking of the one or more historical time-independent health parameters and the one or more converted historical time-independent health parameters; and communicating the recommendation to a computing device for display on the computing device.

15. The system of claim 14, further comprising identifying one or more treatable health parameters from the one or more historical time-independent health parameters and the one or more converted historical time-independent health parameters within the particular cluster.

16. The system of claim 14, further comprising generating a survival percentage of each one or more time-independent health parameters and the one or more converted historical time-independent health parameters, the survival percentage being generated based on an effect treatment of each of the health parameters is predicted to have on the particular patient associated with the particular patient dataset.

17. The system of claim 14, further comprising modeling the one or more historical time-dependent health parameters and the one or more particular time-dependent health parameters using sine and cosine functions.

18. The system of claim 17, wherein the transformation algorithm is a Fourier transform algorithm of the sine and cosine functions.

19. The system of claim 14, wherein the at least one treatable historical health parameter comprises pneumonia.

20. The system of claim 14, wherein converting the one or more historical time-dependent health parameters of the historical patient dataset and the particular patient dataset into the one or more converted historical time-independent health parameters further comprises:

converting the one or more historical time-dependent health parameters from time-dependent data in a time domain to time-independent data in a frequency domain using a Fourier transform algorithm;

computing one or more statistical measures of the time-independent data in the frequency domain; and generating the one or more converted historical time-independent health parameters based at least on the one or more statistical measures of the time-independent data using the fuzzy logic algorithm.

21. The computer-implemented method of claim 1, wherein populating the probabilistic graph database comprises storing weighted connections representing confidences and distances between health parameters derived from the multiple thousands of versions of the analytical dataset, wherein generating the plurality of clusters comprises adjusting similarity thresholds based on the weighted connections to regulate cluster formation.

22. The computer-implemented method of claim 1, wherein populating the probabilistic graph database comprises encoding weighted probabilistic relationships between health parameters based on confidences derived from the multiple thousands of versions of the analytical dataset, wherein generating the plurality of clusters comprises applying a self-organizing map and a k-nearest neighbor algorithm that utilize the weighted probabilistic relationships to determine distances and cluster boundaries.

* * * * *